(12) United States Patent
Davanzo et al.

(10) Patent No.: US 9,925,168 B2
(45) Date of Patent: Mar. 27, 2018

(54) PREPARATION OF MICRONIZED PARTICLES OF AN ANTIMUSCARINIC COMPOUND BY HYDRODYNAMIC CAVITATION

(71) Applicant: CHIESI FARMACEUTICI S.P.A., Parma (IT)

(72) Inventors: Stephen P. Davanzo, Cleveland, OH (US); Barry E. Nall, Cleveland, OH (US); Timothy J. Rouse, Parma (IT); Michele Miozzi, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/409,952

(22) Filed: Jan. 19, 2017

(65) Prior Publication Data
US 2017/0209414 A1 Jul. 27, 2017

(30) Foreign Application Priority Data

Jan. 22, 2016 (EP) ..................... 16152461

(51) Int. Cl.
| | |
|---|---|
| *A61K 31/40* | (2006.01) |
| *A61K 9/00* | (2006.01) |
| *A61K 9/16* | (2006.01) |
| *B01J 19/00* | (2006.01) |
| *B01J 19/06* | (2006.01) |
| *A61M 15/00* | (2006.01) |

(52) U.S. Cl.
CPC ............ *A61K 31/40* (2013.01); *A61K 9/008* (2013.01); *A61K 9/0075* (2013.01); *A61K 9/1694* (2013.01); *A61M 15/0065* (2013.01); *B01J 19/008* (2013.01); *B01J 19/06* (2013.01)

(58) Field of Classification Search
CPC ...................................................... A61K 31/40
See application file for complete search history.

(56) References Cited

U.S. PATENT DOCUMENTS

| | | | | |
|---|---|---|---|---|
| 2002/0183293 | A1* | 12/2002 | Banerjee | ............. A61K 9/0078 514/171 |
| 2008/0227988 | A1* | 9/2008 | Baxter | ................ C07D 207/12 548/556 |
| 2014/0322142 | A1 | 10/2014 | Pasquali et al. | |
| 2015/0352127 | A1 | 12/2015 | Brambilla et al. | |

FOREIGN PATENT DOCUMENTS

| | | |
|---|---|---|
| EP | 2 234 595 | 10/2010 |
| WO | 01/76575 | 10/2001 |
| WO | 2005/105043 | 11/2005 |

OTHER PUBLICATIONS

Find J. et al., "Journal of Materials Research, Materials Research Society", vol. 16, No. 12, Jan. 1, 2001, pp. 3503-3513.
European Search Report issued in Application No. 16152461.6 dated Apr. 7, 2016.
International Search Report dated Mar. 28, 2017 in PCT/EP2017/051405.

* cited by examiner

*Primary Examiner* — Benjamin Packard
(74) *Attorney, Agent, or Firm* — Oblon, McClelland, Maier & Neustadt, L.L.P.

(57) ABSTRACT

Crystalline micronized particulate of a glycopyrronium salt may be prepared by hydrodynamic cavitation. The resulting drug particles are physically stable with regard to agglomeration and/or aggregation on storage.

7 Claims, 3 Drawing Sheets

Fig. 1A
Fig. 1B
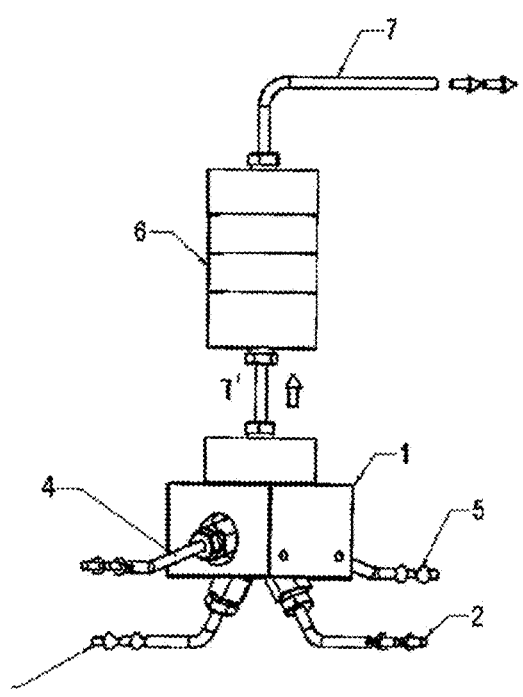
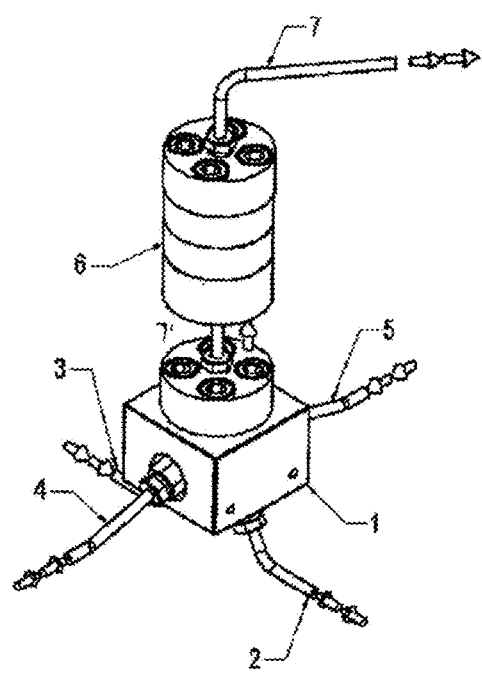

US 9,925,168 B2

PREPARATION OF MICRONIZED PARTICLES OF AN ANTIMUSCARINIC COMPOUND BY HYDRODYNAMIC CAVITATION

CROSS REFERENCES TO RELATED APPLICATIONS

This application claims priority to European Patent Application No. 16152461.6, filed on Jan. 22, 2016, which is incorporated herein by reference in its entirety.

BACKGROUND OF THE INVENTION

Field of the Invention

The present invention relates to processes for the manufacture of crystalline particles of an anti-muscarinic drug. The present invention also relates to Said particles pharmaceutical formulations which contain such particles and methods for the prevention and/or treatment of respiratory diseases by administering such a formulation.

Discussion of the Background

It is known that water soluble quaternary ammonium compounds with antimuscarinic activity tend to agglomerate during storage. This is attributed to the formation of crystal bridges between neighboring particulates due to the absorption of moisture post micronization and subsequent recrystallization of surface amorphous content which is generated by the high energy micronization process. This problem particularly affects the physical stability of the drug and its subsequent performance in formulations.

Glycopyrronium is an anti-muscarinic drug commercially available as bromide salt since many years.

Glycopyrronium bromide has two chiral centers corresponding to four isomeric forms comprising two pairs of diastereoisomers, namely (3S,2'R)-, (3R,2'S)-, (3R,2'R)-, and (3S,2'S)-[(cyclopentyl-hydroxyphenylacetyl)oxy]-1,1-dimethylpyrrolidinium bromide. Commercially available glycopyrronium bromide consists of the purified "threo" diastereoisomer (3R,2'S) and (3S,2'R) and is hereinafter indicated as rac-glycopyrronium bromide.

However, similarly to other anti-muscarinic agents, glycopyrronium salts have significant stability problems, especially immediately following conventional micronization processes by milling.

In fact, glycopyrronium bromide, once micronized, has a strong tendency to aggregate and/or agglomerate, which severely hinders downstream drug processing, particularly the preparation of dry powder formulations for administration by inhalation capable of delivering a good respirable fraction.

Various processes have been proposed in order to change certain physicochemical properties of the drug. However many of these processes involve the use of solvents which tend to cause local solvation processes that, in turn, lead to particle growth and/or irreversible aggregation and agglomeration during drying or storage.

In addition, it is well known that the current state-of-the-art high energy physical processing procedures, such as air jet milling, dry powder ball-milling or high pressure homogenization, give rise to a partial loss of drug crystallinity. These micronized materials are often subjected to post micronization conditioning at high temperature for long periods in order to condition out any process-induced structural disorder and/or amorphous content.

In view of these considerations, it would be highly advantageous to provide a process for preparing crystal particles of a glycopyrronium salt, physically stable, with a narrow particle size suitable for delivery by inhalation.

This problem is solved by the process of the present invention.

SUMMARY OF THE INVENTION

Accordingly, it is one object of the present invention to provide novel processes for preparing crystal particles of a glycopyrronium salt.

It is another object of the present invention to provide novel processes for preparing crystal particles of a glycopyrronium salt, which are physically stable and have a narrow particle size suitable for delivery by inhalation These and other objects, which will become apparent during the following detailed description, have been achieved by the inventors' discovery of the process described below.

Thus, in a first aspect, the present invention provides a process for the preparation of micronized crystallized particles of a pharmaceutically acceptable salt of glycopyrronium, the process comprising:

(a) in a first chamber of a controlled flow hydrodynamic cavitation apparatus, mixing a stream $F_1$ of a solution comprising a pharmaceutically acceptable salt of glycopyrronium and one or more surfactants dissolved in a solvent selected from the group consisting of 1-butanol, 2-propanol and mixtures thereof with ethanol, with one or more streams $F_2$ of an anti-solvent selected from the group consisting of diethyl ether, n-heptane and methyl tert-butyl ether (MTBE) and mixtures thereof;

(b) treating the mixed streams $F_1$ and $F_2$ through a local constriction flow to create controlled flow hydrodynamic cavitation thereby causing nucleation and the direct production of nano-crystals of the salt of glycopyrronium;

(c) transferring the mixed steams to a second chamber of said controlled flow cavitation apparatus and further treating said mixed streams for a time equal or lesser than 10 milliseconds;

(d) collecting the resulting streams in a receiver containing a mixture of n-heptane and MTBE in a ratio ranging from 10:90 v/v to 40:60 v/v, allowing the nanoparticles to assemble;

(e) drying the particles to harden the assembled particles;

(f) eliminating the surfactants; and (g) further drying the obtained micronized particles.

Preferably, the surfactant is selected from the group consisting of lecithin, nonionic surfactants such as Tweens® and Spans®, sugar-based surfactants such as sucrose stearate and sucrose hexadecanoate and mixtures thereof in any ratio.

In a second aspect, the present invention relates to a process for preparing a formulation for inhalation comprising the step of mixing the above micronized particles with one or more propellants or carriers.

In a third aspect, the present invention relates to a pressurized formulation for inhalation comprising the micronized particles of a pharmaceutically acceptable salt of glycopyrronium obtained by the claimed process, suspended in a pressure-liquefied propellant.

In a fourth aspect, the present invention relates to a pressurized metered dose inhaler (pMDI) filled with the aforementioned formulation.

In a fifth aspect, the present invention concerns a dry powder formulation comprising the micronized particles of a pharmaceutically acceptable salt of glycopyrronium obtained by the claimed process with particles of a physiologically acceptable, pharmacologically inert solid carrier.

In a sixth aspect, the invention concerns a dry powder inhaler filled with the aforementioned formulation.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1A and FIG. 1B are frontal (left) and perspective (right) views of the hydrodynamic cavitation apparatus, respectively.

DETAILED DESCRIPTION OF THE PREFERRED EMBODIMENTS

Figure 2:
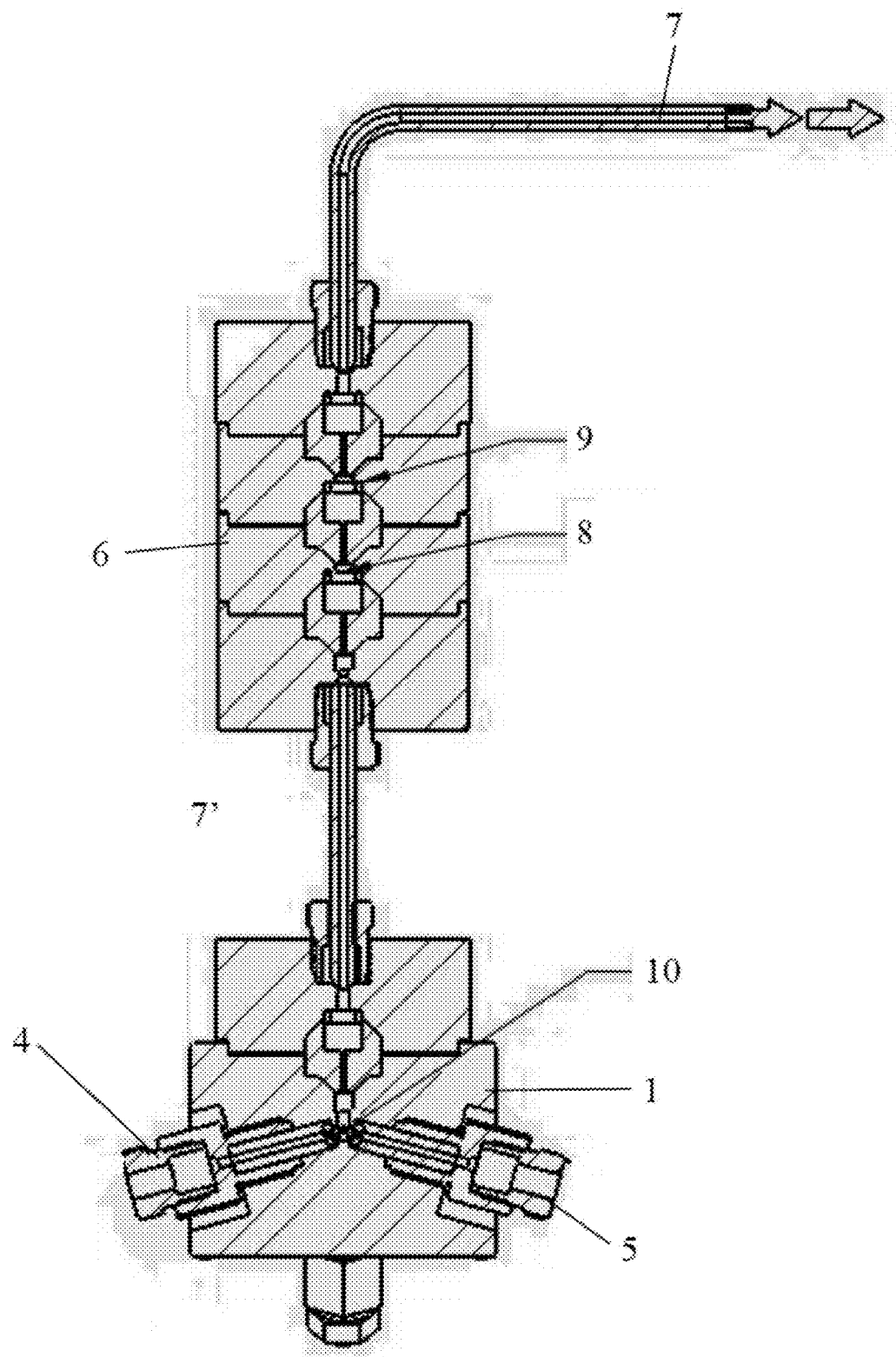
FIG. 2 is a cross-sectional view taken of a longitudinal section of the hydrodynamic cavitation apparatus.

The term "controlled flow hydrodynamic cavitation apparatus" refers to any apparatus suitable to produce microparticles of an organic material. Said devices are known in the art. Cavitation is the formation of bubbles and cavities within a liquid stream resulting from a localized pressure drop in the liquid flow. The paper entitled "Hydrodynamic cavitation as a tool to control macro-, micro- and nano-properties of inorganic materials" by J. Find et al (Journal of Materials Research vol. 16, no. 12, December 2001), which is incorporated herein by reference in its entirety, refers to hydrodynamic cavitation to produce solid-state materials.

The term "micronization" refers to the process of reducing the average diameter of a solid material's particles. Usually, the term micronization is used when the particles that are produced are only a few micrometers in diameter. Traditional micronization techniques are based on the use of friction to reduce particle size. Such methods include milling and grinding. Reduction in particle size may also take place as a result of collision and impact.

The verb "to aggregate" means to assemble or combine together. Freshly micronized drugs tend to take the form of a fine powder that tends to spontaneously coalesce over time to form aggregates of the drug. These aggregates resemble a less fine or even coarse powder.

The verb "to agglomerate" means to form a mass or cluster of particles, particularly in the presence of moisture. Agglomerates of micronized drugs tend on storage, particularly in the presence of moisture, to form a coarse powder, clumps or even a substantially sole mass of drug.

The presence of agglomerates of the drug in the formulation may be detected by a Near Infrared Spectrophotometer provided with a microscope according to known methods.

The term "physically stable" means that, on storage, there is no evidence of particle growth and/or agglomeration of the drug particles.

The size of the drug particles and their agglomeration can be determined according to methods known to the skilled person in the art.

One particular apparatus that can be used is the Sympatec Dry Dispersion Size Analyzer.

The term "chemically stable" refers to a drug that, upon storage, meets the requirements of the EMEA Guideline CPMP/QWP/122/02 referring to "Stability Testing of Existing Active Substances and Related Finished Products" which is incorporated herein by reference in its entirety.

The term "anti-solvent" means a liquid having little or no solvation capacity for the drug. The solubility of the drug in the anti-solvent should be less than about 1 mg/ml determined according to known methods. Preferably, the solubility of the drug should be less than about 100 µg/ml. More preferably, the solubility of the drug should be less than about 10 µg/ml.

The term "water immiscible" means that less than 100 ppm, and preferably less than 10 ppm, of water can dissolve in the anti-solvent. The amount of residual water can be determined according to known methods, such as Karl-Fischer.

The term "conditioning" means the exposure of the powder to a combination of temperature and relative humidity controlled conditions.

The "particle size" is the Gaussian distribution of the diameter of particles.

Said particle size can be quantified by measuring the volume diameter by laser diffraction using suitable known instruments such as, for instance, the Malvern or Sympatec apparatus.

The volume diameter (VD) is related to the mass diameter (MD) by the density of the particles (assuming a size independent density for the particles).

The particle size is expressed in terms of volume diameter and the particle size distribution is expressed in terms of d(v0.5), which corresponds to the diameter of 50 percent by volume of the particles and, also in terms of d(v0.9) and d(v0.1) which express the values under which 90% of particles and 10% of the particles of a sample have a lower volume diameter, respectively.

Upon aerosolization, the particle size is expressed as mass aerodynamic diameter (MAD) and the particle size distribution as mass median aerodynamic diameter (MMAD). The MAD indicates the capability of the particles of being transported suspended in an air stream. The MMAD corresponds to the mass aerodynamic diameter of 50 percent by weight of the particles.

The term "good flowability" refers to a formulation that is easy handled during the manufacturing process and is able to ensure an accurate and reproducible delivering of the therapeutically effective dose.

Flow characteristics can be evaluated by different tests such as angle of repose, Carr's index, Hausner ratio or flow rate through an orifice.

The term "good homogeneity" refers to a formulation wherein, upon mixing, the uniformity of distribution of the active ingredient, expressed as coefficient of variation (CV) also known as relative standard deviation (RSD), is equal to or less than 5.0%.

The term "respirable fraction" refers to an index of the percentage of active particles which would reach the deep lungs in a patient.

The respirable fraction, also referred to as fine particle fraction (FPF), is evaluated using a suitable in vitro apparatus such as Andersen Cascade Impactor (ACI), Multi Stage Liquid Impinger (MLSI) or Next Generation Impactor (NGI), preferably by ACI, according to procedures reported in common Pharmacopoeias, in particular in the European Pharmacopeia (Eur. Ph.) 7.3, $7^{th}$ Edition, which is incorporated herein by reference in its entirety. It is calculated by the percentage ratio between the fine particle mass (formerly fine particle dose) and the delivered dose.

The delivered dose is calculated from the cumulative deposition in the apparatus, while the fine particle mass is calculated from the deposition of particles having a diameter<5.0 micron.

The present invention is directed to a process for the preparation of micronized crystallized particles of a glycopyrronium pharmaceutically acceptable salt by means of controlled flow hydrodynamic cavitation to effect nucleation in the crystallization step.

It has been found that, by operating according to the conditions disclosed hereinafter, a physically stable crystalline powder of a glycopyrronium pharmaceutically acceptable salt, with particles having a narrow size suitable for inhalation, could be obtained.

In particular, it has been found that the drug particles obtained by the process of the invention are stable so that they are resistant to aggregation and/or to agglomeration. In other words, the tendency of the resulting dry micronized material to aggregate and/or agglomerate post processing is minimized or completely avoided.

Said drug particles also show better flow properties compared to traditional jet milled micronized material.

Advantageously, any organic or inorganic pharmaceutically acceptable salt of glycopyrronium may be used. Organic salts may comprise, for instance, formate, acetate, trifluoroacetate, propionate, butyrate, lactate, citrate, tartrate, malate, maleate, succinate, methanesulfonate, benzenesulfonate and benzoate, while inorganic salt may include, but are not limited to, fluoride chloride, bromide, iodide, phosphate, nitrate and sulphate.

Preferably, an inorganic salt is used selected from the group consisting of fluoride, chloride, bromide, and iodide, preferably chloride or bromide, even more preferably bromide.

Glycopyrronium may be used in the form of any of the pure enantiomers or diastereoisomers or any combination thereof.

(3S,2'R), (3R,2'S)-3-[(Cyclopentylhydroxyphenylacetyl)oxy]-1,1-dimethylpyrrolidinium bromide racemic mixture, also known as rac-glycopyrronium bromide, is preferably used.

FIG. 1A and FIG. 1B illustrate a hydrodynamic cavitation apparatus suitable to perform the process of the invention. FIG. 2 illustrates its cross-sectional view.

The apparatus of FIG. 1A and FIG. 1B comprises a first chamber 1 and four inlets for introducing fluid streams $F_1$ into said chamber and a first outlet 7' for transferring the fluid into a second chamber 6.

The second chamber 6 comprises two inner mixing zones 8 and 9 (see FIG. 2) and a second outlet 7 for exiting the fluid.

More details of the apparatus are disclosed in the co-pending U.S. patent application Ser. No. 14/216,188, which is incorporated herein by reference in its entirety.

Although it is preferred that the cross-section of the first chamber 1 is rectangular, while that of the second chamber 6 is cylindrical, both chamber may have any geometric shape such as square or hexagonal without departing from the scope of the invention.

Cavitation generators such as orifices are provided along or near the centerline within the first chamber 1.

The orifices are positioned such that all flows converge on a single point. In place of disk having orifices, it is possible to use a crosshead, post-propeller or any other fixture that produces a minor loss of pressure.

The orifices are configured to generate a hydrodynamic cavitation field downstream from baffle via a local constriction of fluid flow. In this embodiment, the orifices are holes drilled in a circular disk.

Although local constriction is an annular orifice, a skilled person would understand that if the cross-section of flow-through channel is of any other geometric shape other than circular, then the local constriction defined between the wall forming flow-through channel and baffle may not be annular in shape.

Likewise, if an orifice is not circular in cross-section, then the local constriction may not be annular in shape. Preferably, the cross-sectional geometric shape of the first chamber matches the cross-sectional geometric shape of baffle (e.g., circular-circular, square-square, etc.).

To further promote the creation and control of cavitation fields downstream from orifice, the orifice is constructed to be removable and replaceable by any orifice having a variety of shapes and configurations to generate varied controlled flow hydrodynamic cavitation fields. The shape and configuration of orifice can significantly affect the character of the cavitation flow and, correspondingly, the quality of crystallization.

Although there are an infinite variety of shapes and configurations that can be utilized within the scope of this invention, several acceptable baffle shapes and configurations are disclosed in U.S. Pat. No. 7,314,516 which is incorporated herein by reference in its entirety.

It is understood that orifice can be removably mounted to stem in any acceptable fashion.

In operating the apparatus illustrated in FIG. 1A and FIG. 1B, a first fluid stream $F_1$ consisting of a solution comprising a pharmaceutically acceptable salt of glycopyrronium and one or more surfactants dissolved in a suitable solvent enters the first chamber 1 via inlet 2 and moves through orifices in disk in the direction of the point of convergence. A second fluid stream $F_2$ consisting of a suitable anti-solvent enters the first chamber 1 via one or more inlets 3, 4 and 5, and mixes with the first fluid stream $F_1$ at the point of convergence (crystallization zone, 10).

The above indications about the inlets to be used are only exemplary as they are exchangeable.

Advantageously, the total flow of anti-solvent is divided across the three inlets 3, 4 and 5 in any ratio.

Preferably, the total flow of anti-solvent is divided in a ratio of 40%:30%:30 across the three inlets 3, 4 and 5.

The pressures, temperatures and flow rates shall be varied along the four inlets according to the knowledge of the skilled person in the art.

Advantageously, the temperature of all the inlets is maintained at room temperature. More advantageously the pressure of inlet 1 is maintained at 400-600 psi, preferably 500 psi, while that of the three inlets 3, 4 and 5 is maintained at 2500-5000 psi.

In a preferred embodiment, the flow rate of the glycopyrronium solution is maintained at 10-15%, more preferably 12%, of the total flow rate of the anti-solvent.

The mixed first and second fluid streams i.e. $F_1$ and $F_2$, then pass through local constriction of flow, where the velocity of first and second fluid streams i.e. $F_1$ and $F_2$, increases to a minimum velocity (i.e. a velocity at which cavitation bubbles begin to appear) dictated by the physical properties of the first and second fluid streams i.e. $F_1$ and $F_2$. As the first and second fluid streams, i.e. $F_1$ and $F_2$ pass through local constriction of flow, hydrodynamic cavitation field (which generates cavitation bubbles) is formed downstream of baffle.

The tiny crystals containing-fluid exits the first chamber 1 via the outlet 7' and enters into the second chamber 6 with two additional mixing zones 8, 9 to allow for longer residence time and allowing additional mixing of the solvent and anti-solvent.

Advantageously, the tiny crystals containing-fluid remains in said second mixing chamber for a time comprised between 1 and 5 milliseconds, preferably 2-3 milliseconds.

The permanence of the steams in the first chamber as well as in the mixing zones of the second chamber shall be adjusted by the person in the art according to its knowledge and depending on the desired particle size.

The two fluids used in this process are of different solvent composition, one fluid being a solution of the compound to be processed in a suitable solvent or combination of solvents ("feed solution"), and the other fluid being a suitable solvent or combination of solvents capable of initiating that compound's precipitation from solution ("anti-solvent"), chosen for its relatively low solvation property with respect to that compound.

Advantageously, the solvent is selected from the group consisting of 1-butanol, 2-propanol and mixtures thereof with ethanol in any ratio. Preferably the solvent is 2-propanol.

The solvent used in the process of the present invention also comprises suitable surfactants which alleviate agglomeration that might occur during the hydrodynamic cavitation crystallization process and allow surfactant self-assembly of particles with the targeted particle size.

The concentration of the glycopyrronium salt in stream F1 is suitably 0.5% to 5.0% w/w, preferably 1.0 to 2.0% w/w, based on the total weight of the solution.

Advantageously, the surfactant is present in a weight ratio ranging from 70:30 to 30:70 with respect to the amount of glycopyrronium salt, preferably from 65:35 to 55:45 w/w, more preferably of 62:38 w/w.

The surfactant may be selected from the group of lecithins of any source such as soy, non-ionic surfactants such as tweens (polysorbates) and spans (sorbitan esters), sugar-based surfactants such as sucrose stearate and sucrose hexadecanoate, and mixtures thereof in any ratio.

A mixture of lecithin and span 60 could preferably be used, preferably in a 50:50 w/w ratio.

In another preferred embodiment, only lecithin may be used.

In a further preferred embodiment a mixture of soy lecithin, sorbitan monostearate (span) 60 and sucrose stearate could be used, more preferably in a ratio of 47:47:6 w/w/w.

Advantageously, the anti-solvent is selected from the group consisting of diethyl ether, n-heptane, and methyl tert-butyl ether (MTBE) and mixtures thereof, in any ratio.

Advantageously, the anti-solvent is a mixture of n-heptane and MTBE in any ratio in a ratio ranging from 20:80 v/v to 30:70 v/v, even more preferably in a ratio of 25:75 v/v.

In a particular embodiment, MTBE alone could be used.

Usually, the mixed stream exiting the second chamber 6 from the outlet 7, contains particles of the glycopyrronium salt having a particle size equal to or lesser than 100 nm, preferably of 50-70 nm.

Said fluid stream is collected in a suitable receiver such as a stirred stainless steel tank with temperature control, containing a mixture of n-heptane and MTBE in a ratio ranging from 10:90 v/v to 40:60 v/v, preferably from 20:80 v/v to 30:70 v/v, more preferably in a ratio of 25:75 v/v.

The particles are mixed inside the receiver for a short time, usually less than 30 minutes, preferably less than 15 minutes.

Generally, the time of mixing shall be adjusted by the skilled person in the art to achieve the desired particle size in microns.

The product is isolated and harvested using conventional recovery techniques.

For instance, the above preferred surfactants are soluble in n-heptane.

Therefore, in a preferred embodiment of the invention, the fluid containing the particles of the glycopyrronium salt is first filtered. Then the collected particles are dried and re-suspended in n-heptane, mixed, for instance for one hour, filtered again, washed a second time with n-heptane and finally dried, for instance at 50° C. under vacuum.

Advantageously, the total amount of surfactants in the final product is less than 5% w/w, more advantageously less than 1%, preferably equal to or less than 0.1%, even more preferably equal to or less than 0.01% w/w.

Advantageously, the collected particles of glycopyrronium salt shall be nominally crystalline such that the atoms or molecules are arranged in a regular, periodic manner. However, the crystalline drug may contain some amorphous regions. Preferably, the drug should have a crystallinity equal to or higher than 90% or, more preferably, higher than 95%, more preferably higher than 98% as determined according to known methods.

All the obtained particles of the glycopyrronium salt shall have a volume diameter comprised between 0.5 microns and 15 microns.

Advantageously, at least 90% of the obtained particles d(v0.9) should have a diameter of less than 10 micron, preferably of less than 8 micron, more preferably of less than 7 micron. Advantageously, the d(v0.5) is comprised between 1 and 5 micron, more advantageously between 1.5 and 4 micron, preferably between 2 and 3 micron. More preferably, no more than 10% of all glycopyrronium particles have a diameter lower than 0.6 micron, even preferably equal to or lower than 0.8 micron.

In this context, the particle size is determined as volume diameter according to known methods such as laser diffraction based on the use of suitable apparatus such as Mastersizer apparatus (Malvern Instruments Ltd, Worcestershire, UK) or Dry Dispersion Size Analyzer (Sympatec GmbH, Clausthal-Zellerfeld, Germany).

In general, drug particles of this size are suitable for administration by inhalation. In fact particles having a particle size greater than about 10 microns are likely to impact the walls of the throat and generally do not reach the lung.

Advantageously, the micronized crystalline drug particles obtained with the process of the invention could be physically and chemically stable for at least one month under ambient conditions (22±2° C. and 60% relative humidity). Preferably, said micronized particles could be stable for at least 3 months at the same ambient conditions.

The physical stability shall be measured by using a Sympatec Dry Dispersion Size Analyzer, while the chemical stability shall be determined according to known method such as HPLC.

Alternatively, the physical stability may be measured using the specific surface area of the drug particles analyzed by adsorption analysis, BET surface measurement, according to a method known in the art.

Optionally, to further reduce the tendency of the glycopyrronium salt to aggregate and/or agglomerate during storage, the particles obtained with the process of the present invention may be subjected to a conditioning step according to the conditions reported in EP 2 234 595, which is incorporated herein by reference in its entirety, but for much shorter time (less than one hour).

Alternatively, said particles may be subjected to conditioning by loading them in a rotating drum with a wet conditioning gas. The particles will then be suspended in this moving conditioning chamber for a short time, for instance 1 to 30 minutes. The rotating tube allows the particles to stay far enough apart that they do not agglomerate during the conditioning step. This conditioning approach is significantly faster than typical environmental conditioning which can take several days or weeks.

Particles of glycopyrronium salts obtained in accordance with the process of the present invention can be admixed with propellants or carrier particles, thus providing formulations having a good homogeneity.

Therefore, the present invention also encompasses formulations suitable for administration by inhalation comprising the glycopyrronium particles obtainable with the process of the invention in combination with one or more drugs useful for the treatment of respiratory disease, for example, short-acting and long-acting beta$_2$-agonists such as terbutaline, salmeterol, formoterol, milveterol, indacaterol, olodaterol, and fenoterol, corticosteroids such as rofleponide, flunisolide budesonide, ciclesonide, mometasone and its ester, i.e. furoate, fluticasone and its ester, i.e. propionate and furoate.

In particular, in one embodiment, the present invention encompasses inhalable pressurized formulations in form of suspension of the aforementioned micronized particles in a pressure-liquefied propellant, preferably a hydrofluoroalkane (HFA) propellant selected from the group of 1,1,1,2-tetrafluoroethane (HFA134a), 1,1,1,2,3,3,3-heptafluoro-propane (HFA227) and any mixtures thereof.

In another embodiment, the present invention encompasses inhalable dry powder formulations comprising the aforementioned micronized particles in admixture with particles of a physiologically acceptable pharmacologically-inert solid carrier, such as lactose, preferably alpha-lactose monohydrate and optionally with further additives such as magnesium stearate.

Said formulations can be administered by suitable devices such as pressurized metered dose inhalers (pMDIs) or dry powder inhalers (DPIs).

The micronized particles obtainable with the process of the invention may be used for prophylactic purposes or for symptomatic relief for a wide range of conditions including: respiratory disorders such as chronic obstructive pulmonary disease (COPD) and asthma of all types. Other respiratory disorders for which the product of the invention may be beneficial are those characterized by obstruction of the peripheral airways as a result of inflammation and presence of mucus, such as chronic obstructive bronchiolitis, chronic bronchitis, emphysema, acute lung injury (ALI), cystic fibrosis, rhinitis, and adult or respiratory distress syndrome (ARDS).

In addition, said particles may be useful in treating smooth muscle disorders such as urinary incontinence and irritable bowel syndrome; skin diseases such as psoriasis; hyperhidrosis, and gastrointestinal ulcers.

The dosage of the glycopyrronium salt will depend on the type and severity of the disease/condition as well as the sex and age of the patient to be treated. Therefore it will be determined by the skilled artisan accordingly. In some embodiments, the daily dosage could advantageously be 6 to 100 microg, preferably 12 to 50 microg.

Other features of the invention will become apparent in the course of the following descriptions of exemplary embodiments which are given for illustration of the invention and are not intended to be limiting thereof.

EXAMPLES

Example 1. Preparation of a Micronised Powder of Rac-Glycopyrronium Bromide

The process was carried out using the apparatus of FIG. 1A and FIG. 1B. 6 grams of rac-glycopyrronium bromide and 9.75 grams of a mixture of soy lecithin:span 60:sucrose stearate 47:47:6 w/w/w were dissolved in 400 ml of 2-propanol (solution A). The obtained solution A entered the first chamber 1 via inlet 2 and was maintained at a temperature of 50° C. and a pressure of 500 psi.

The anti-solvent n-heptane entered in the same chamber 1 from the inlets 3,4, and 5 and the total flow, maintained at a temperature of 25° C. at a pressure of 5000 psi, was divided approximately 40%:30%:30% across the three inlets.

The flow rate of solution A was maintained at about 12% of the total flow of the anti-solvent.

The glycopyrronium solution and anti-solvent were then passed though orifices causing hydrodynamic cavitation to effect nucleation. The pressure was maintained at 5000 psi.

The four streams mixed at the point of convergence wherein controlled flow hydrodynamic cavitation caused nucleation. Then the mixed streams exited the chamber 1 via the outlet 7' and entered the second chamber 6, maintained at a pressure 5000 psi, undergoing two more mixing zones for a period of 2 milliseconds. The stream exited the second chamber 6 through the outlet 7 and were collected in a receiver which contains heptane/MTBE at a ratio of 25%/75% v/v. The receiver was maintained at a constant ratio of heptane MTBE by a metering pump. The mixture was allowed to mix gently in the receiver for approximately 5 minutes.

The obtained particles were filtered out using a Millipore pressure filter. Then they were vacuum dried, re-suspended in n-heptane at 60° C., mixed for one hour, and filtered again. The washing procedure was repeated three times.

The amount of residual surfactants turned out to be of less than 4% w/w.

Resulting material was then tested as reported in Example 2.

Example 2. Analysis of Rac-Glycopyrronium Bromide Powder Material of Example 1

The microparticles as obtained in Example 1 were characterized in terms of morphology, drug content, crystallinity, density, hygroscopicity, and particle size.

Figure 3:
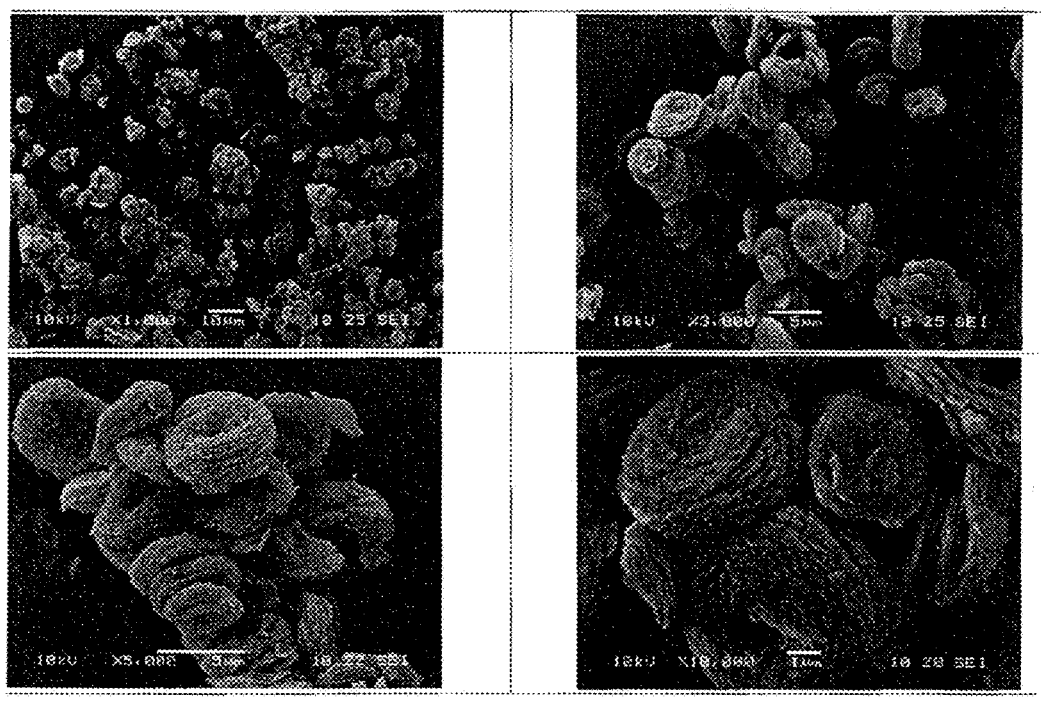
FIG. 3 shows different magnifications of the SEM pictures of the rac-glycopyrronium bromide particles.

The morphology of the microparticles was determined by scanning electron microscope (SEM) using a JSM-6480LV instrument (JEOL Ltd, Tokyo, Japan). Examination showed an unusual morphology in a flower petal arrangement (see FIG. 3).

The drug content was determined by UPLC-PDA assay. No degradation/impurities peaks were detected above the limit of detection of the analytical method at the release and/or after 3 months.

The crystallinity was determined by differential scanning calorimetry (DSC) using a Q2000 apparatus (TA Instruments, New Castle, Del.). The temperature was ramped 10° C. min$^{-1}$ up to 250° C. The sample showed a clear sharp melt at 191.5° C. followed by the onset of degradation. Due to the highly crystalline nature of the sample, no glass transition was observed. This was confirmed by powder XRD diffraction.

The water sorption properties were determined by dynamic vapor sorption (DVS) using a Q5000SA apparatus (TA Instruments, New Castle, Del., USA). The sorption cycles were measured by ramping directly from 10% r.h. (relative humidity) to 90% r.h. with an initial equilibration time of 60 minutes at 0% r.h.

The behavior was typical of a crystalline material with a low moisture uptake of less than 2.5%.

The density of the powder was measured by helium picnometry using a AccPyc II 1340 instrument (Micromeritics, Milan, Italy). The mean value calculated from triplicate measurements was 1.3917 g/cm$^3$.

The particle size was determined by Laser light diffraction using the Sympatec Dry Dispersion Size Analyzer (Clausthal-Zellerfeld, Germany).

The powder was dispersed for two measurement conditions at an air pressure of 1 and 4 bar.

The average d[v,10], d[v,50], d[v,90] values were calculated from triplicate measurements. The span was calculated using the following equation:

$$\text{Span} = [d(v,0.9) - d(v,0.1)]/d(v,0.5)$$

The values obtained for particle size, which are reported in Table 1, were not significantly affected by the dispersion pressure, indicating a free flowing powder with no hard aggregates.

TABLE 1

| Dispersion pressure (bar) | d[v,10] | d[v,50] | d[v,90] | Span |
|---|---|---|---|---|
| 1.0 | 0.81 | 4.17 | 7.05 | 1.50 |
| 4.0 | 0.43 | 2.29 | 5.45 | 2.19 |

No significant growth of the particle size was observed upon storage for at least three months under ambient conditions (22±2° C. and 60% relative humidity).

Example 3. Preparation of a Dry Powder Formulation Wherein the Active Ingredient is Rac-Glycopyrronium Bromide Alpha-lactose monohydrate SpheroLac 100 (Meggle) and magnesium stearate in the ratio of 98:2% by weight were co-milled in a jet mill apparatus (hereinafter the pre-blend). This pre-blend was then mixed with alpha-lactose monohydrate CapsuLac (212-355 microns) in a Turbula mixer for 4 hours at 32 rpm (hereinafter the Carrier). Micronized rac-glycopyrronium bromide as obtained in Example 1 was added to the Carrier and mixed in a Turbula mixer for 120 minutes at 32 rpm to obtain a ratio of 12.5 µg of active to 10 mg of carrier (blend A).

The formulation is assessed for satisfactory bulk powder content uniformity (RSD of 1.1%).

An amount of powders for inhalation was loaded in the multidose dry powder inhaler NEXThaler® (Chiesi Farmaceutici SpA, Italy).

The aerodynamic assessment of particle size distribution was obtained by using a Next Generation Impactor (NGI) following the procedure detailed in the European Pharmacopeia (European Pharmacopoeia 7th Edition: 278-82, which is incorporated herein by reference in its entirety). The following parameters, were calculated: i) the delivered dose (DD) which is the amount of drug delivered from the device recovered in all the parts of impactor; ii) the fine particle mass (FPM) which is the amount of delivered dose having a particle size equal to or lower than 5.0 micron; iii) the fine particle fraction (FPF) which is which is the ratio between the fine particle mass and the delivered dose; iv) the MMAD±GSD; and v) the extrafine FPF which is the percentage of the fine particle mass having a particle size equal to or lower than 1.0 micron. The results (mean value, n=6) are reported in Table 2.

TABLE 2

| | DD (µg) | FPM (µg) | FPF (%) | MMAD (µm) | FPF < 1 µm |
|---|---|---|---|---|---|
| Sample | 22 | 8.1 | 36.6 | 3.7 | 5.3 |

The results show a good delivered dose, indicating that is no significant retention in the DPI device. The fine particle fraction is also satisfactory.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for the preparation of micronised particles of a pharmaceutically acceptable salt of glycopyrronium, said process comprising:
   (a) mixing, in a first chamber of a controlled flow hydrodynamic cavitation apparatus, (i) a stream $F_1$ of a solution comprising a pharmaceutically acceptable salt of glycopyrronium and one or more surfactants dissolved in a solvent selected from the group consisting of 1-butanol, 2-propanol and mixtures thereof with ethanol, with (ii) one or more streams $F_2$ of an antisolvent selected from the group consisting of diethyl ether, n-heptane and methyl tert-butyl ether and mixtures thereof to obtain a mixed stream of $F_1$ and $F_2$;
   (b) passing said mixed stream of $F_1$ and $F_2$ through a local constriction flow to create controlled flow hydrodynamic cavitation thereby causing nucleation and the direct production of nano-crystals of the salt of glycopyrronium;
   (c) transferring said mixed steam of $F_1$ and $F_2$ to a second chamber of said controlled flow cavitation apparatus, and further treating said mixed streams for a time of less than 10 milliseconds;
   (d) collecting the resulting stream in a receiver containing a mixture of n-heptane and MTBE in a ratio ranging from 10:90 v/v to 40:60 v/v, allowing the nanoparticles to assemble, to obtain assembled particles;
   (e) drying said assembled particles to harden said assembled particles;
   (f) removing said one or more surfactants; and
   (g) further drying the obtained micronized particles.

2. The process according to claim 1, wherein said pharmaceutically acceptable salt of glycopyrronium is the bromide salt.

3. The process according to claim 1, wherein said one or more surfactant is selected from the group consisting of lecithin, a nonionic surfactant, a sugar-based surfactant, and mixtures thereof in any ratio.

4. The process according to claim 1, wherein said solvent is 2-propanolol.

5. The process according to claim 1, wherein said anti-solvent is n-heptane.

6. The process according to claim 1, wherein said surfactant is a mixture of soy lecithin, sorbitan monostearate 60, and sucrose stearate.

7. A process for preparing a formulation for inhalation, comprising mixing micronized particles prepared by a process according to claim 1 with one or more propellants or carriers.

* * * * *